United States Patent [19]
Bierman

[11] Patent Number: 5,318,546
[45] Date of Patent: Jun. 7, 1994

[54] METHOD OF CATHETER IRRIGATION AND ASPIRATION

[76] Inventor: Steven F. Bierman, 143 Eighth St., Del Mar, Calif. 92014

[21] Appl. No.: 936,830

[22] Filed: Aug. 28, 1992

[51] Int. Cl.$^5$ .............................................. A61M 5/00
[52] U.S. Cl. .................................. 604/250; 128/898; 251/6; 251/10
[58] Field of Search ............... 604/34, 250, 28, 35; 251/4, 6, 7, 9; 128/10, 898

[56] References Cited

U.S. PATENT DOCUMENTS

| | | |
|---|---|---|
| 3,602,227 | 8/1971 | Andrew . |
| 3,847,370 | 11/1974 | Engelsher ............................. 251/6 |
| 3,942,228 | 3/1976 | Buckman et al. ................ 251/10 X |
| 4,097,020 | 6/1978 | Sussman ............................. 251/10 |
| 4,126,132 | 11/1978 | Portner et al. . |
| 4,266,751 | 5/1981 | Akhavi ................................. 251/6 |
| 4,364,383 | 12/1982 | Vcelka . |
| 4,428,383 | 1/1984 | DeVroom . |
| 4,515,687 | 5/1985 | Bresson et al. . |
| 4,573,974 | 3/1986 | Ruschke . |
| 4,589,626 | 5/1986 | Kurtz et al. ......................... 251/10 |
| 4,621,647 | 11/1986 | Loveland . |
| 4,673,161 | 6/1987 | Flynn et al. ......................... 251/10 |
| 4,781,687 | 11/1988 | Wall . |
| 4,795,429 | 1/1989 | Feldstein . |
| 4,798,590 | 1/1989 | O'Leary et al. . |
| 4,802,650 | 2/1989 | Stricker . |
| 4,834,702 | 5/1989 | Rocco ................................. 604/43 |
| 4,852,844 | 8/1989 | Villaveces . |
| 4,934,375 | 6/1990 | Cole et al. . |
| 5,014,750 | 5/1991 | Winchell et al. . |
| 5,033,714 | 7/1991 | Winchell et al. . |
| 5,035,399 | 7/1991 | Rontanen-Lee ..................... 251/10 |

OTHER PUBLICATIONS

Photographs A–D of a clamp sold by Halkey-Roberts.
Photographs E–H of a clamp sold by Halkey-Roberts.

Primary Examiner—John D. Yasko
Assistant Examiner—Corrine Maglione
Attorney, Agent, or Firm—Knobbe, Martens, Olson & Bear

[57] ABSTRACT

A catheter irrigation device, readily attached to a fluid supply line connected to an indwelling catheter, is used to dislodge clots or blockages at the distal end of the catheter. The irrigation device comprises a pair of opposing rollers configured and positioned such that the fluid supply can be interposed between the rollers. The irrigation device further includes a flexible linkage which supports the rollers and maintains the rollers about the fluid supply tube. The flexible linkage is configured to receive the fluid supply tube and configured to deflect to cause the rollers to pinch the fluid supply tube, thus creating an occlusion. The flexible linkage and roller are further configured to slide over the fluid supply tube, such that with the rollers creating an occlusion in the tube, the irrigation device is slid for a sufficient distance toward the catheter to sufficiently increase the fluidic pressure within the catheter to dislodge the blockage. Alternatively, the device can be slid proximally for a sufficient distance to sufficiently decrease the fluidic pressure within the catheter to dislodge the blockage.

21 Claims, 5 Drawing Sheets

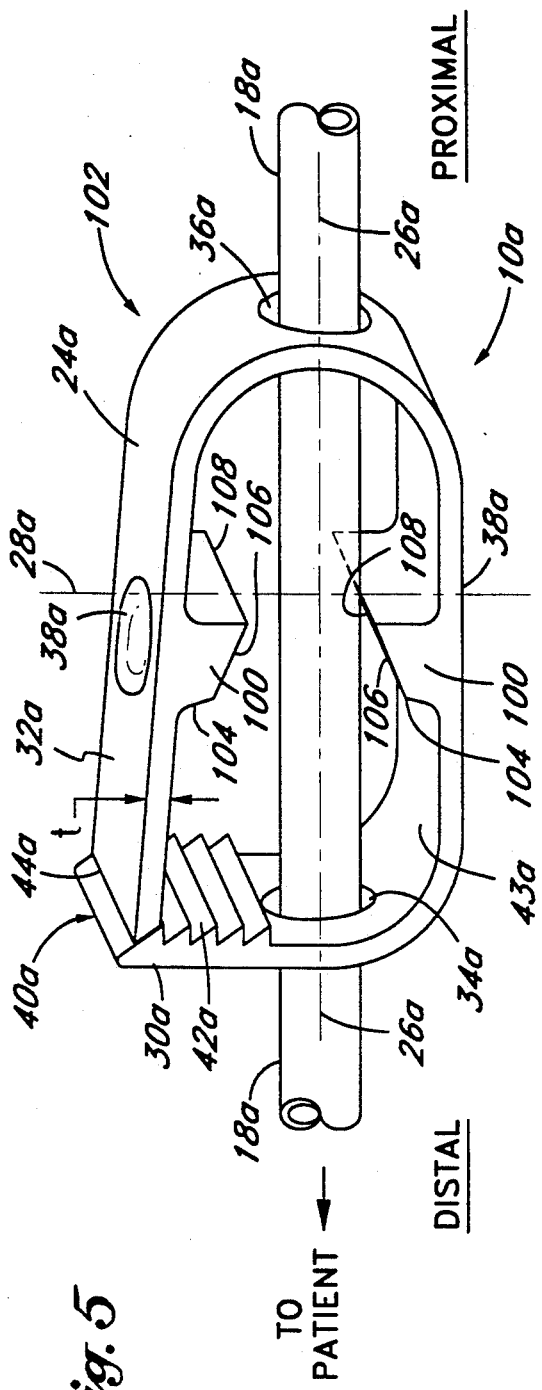

METHOD OF CATHETER IRRIGATION AND ASPIRATION

BACKGROUND OF THE INVENTION

1. Field of the Invention

The present invention relates to percutaneous catheterization systems, and more particularly to a device for and method of irrigating catheterization systems.

2. Description of Related Art

Intravenous ("IV") catheters are commonly used in the treatment of patients to introduce fluids directly into the bloodstream of the patient. In IV catheterization, a supply of fluid, maintained in a container, is typically located above the patient. A catheter supply tube carries the fluid from the container to a catheter attached to patient, thus introducing the fluid into the patient. The catheter is typically inserted in a vein located on the lateral side of the patient's hand or a vein located on the medial side of the arm. The catheter, however, may alternatively be introduced into another body lumen, such as, for example, an artery or an organ.

Typically, a nurse introduces a needle or other stylet through the cannula portion of the catheter and into the skin of the patient at a desired location. The nurse subsequently removes the needle after the cannula is inserted into the body lumen. Fluid flows directly into the lumen (e.g., vessel) of the patient with the fluid supply tube placing the catheter in fluidic communication with the fluid supply container. Gravity and the pressure generated by the head of the fluid above the patient produces fluid flow into the body lumen.

Flow through the catheter, however, may cease because the head of the liquid above the patient is insufficient to force the fluid into the vessel of the patient, as typically is the case when the fluid supply container has fully drained. Flow may also cease when a nurse or like healthcare provider clamps off the flow to administer medication through a "Y"-site port commonly located on the distal side of the clamp. As used herein, "proximal" and "distal" are used in reference to the proximity of the fluid supply container.

When the IV flow stops, blood clots may form and/or other organic debris may deposit on the distal end of the catheter cannula, thus clogging the catheter. Blood clotting occurs within 2 to 3 minutes after the IV flow ceases, and the clot increases in size thereafter.

Because the catheter commonly remains in place during the catheterization period, which typically is maintained for at least several days (depending upon the condition of the patient), the nurse must unclog the catheter by irrigation. That is, the nurse forces fluid through the catheter under sufficient pressure to displace the blockage (i.e., the blood clot or organic debris).

Nurses commonly irrigate the catheterization site using a syringe. The nurse first fills the syringe with liquid from the IV line and then clamps off a section of the fluid supply tube filled with liquid proximate to the indwelling catheter. The nurse inserts the needle of the syringe into the line communicating with the catheter and injects the fluid into the line to increase the fluidic pressure within the catheter to a level greater than that required to dislodge the blockage.

Although this method may be effective, it suffers from several drawbacks. The method exposes the nurse or like healthcare provider to contaminated medical sharps which raises the possibility of the sharp (e.g., the needle of the syringe) sticking the nurse. On average, this exposure occurs at least twice a day. If the syringe needle does stick (or prick) the nurse, he or she as must undergo a series of inoculations, as well as undergo a series of test together with the patient to determine among other things whether the patient is HIV (Human Immunodeficiency Virus) positive. Such inoculations and tests pose substantial expense to hospitals and clinics.

Moreover, the nurse must retrieve a syringe after noticing that the IV flow has stopped. As mentioned above, blood clots within 2 to 3 minutes and the clot increases in size each minute thereafter. Thus, during the time the nurse retrieves the syringe, the blood clot grows, becoming more difficult to dislodge. In addition, the time expended retrieving the syringe adds to administrative costs, thus increasing the cost of healthcare.

This irrigation procedure also causes substantial discomfort to the patient. Nurses typically use large syringes (e.g. 3 to 12 cubic centimeters) to irrigate the catheterization site which raises the pressure within the catheter above the pressure required to dislodge the blockage. A substantial amount of fluid thus flows into the body lumen when the block dislodges, causing the vessel to swell or causing damage to the lining of the vessel, which adds to the patient's discomfort. Further, this irrigation process may lead to inflammation of the vein (Phlebitis), to Thrombophlebitis, or to subcutaneous infiltration (i.e, perforation of vessel wall). The latter consequence necessitates changing of the catheter insertion site, creating further discomfort to the patient and adding administrative expense. Thus, the present irrigation method, by crudely raising the fluidic pressure beyond that which is required to dislodge the blockage, unnecessarily pains the patient and often damages the catheterized vessel.

SUMMARY OF THE INVENTION

In view of the foregoing disadvantages of the currently prevalent method for irrigating catheterization sites, it is apparent that a need exists for an apparatus to irrigate an indwelling catheter, wherein the apparatus is integral to the catheterization system so as to be readily accessible and does not expose the healthcare provider to contaminated sharps. In addition, the related method of using the apparatus should not substantially discomfort the patient.

One aspect of the present invention involves a catheter irrigation device used to dislodge blood clots and/or other organic debris blockages which clog a distal end of an indwelling catheter. The catheter irrigation device attaches to an IV line and remains unobtrusively in place for ready use when required to irrigate the catheterization site. In addition, the catheter irrigation device does not contact the fluid within the IV line nor any body fluid of the patient, and thus is not contaminated during use.

The catheter irrigation device comprises a pair of opposing projections spaced apart from each other to define a space of sufficient size to receive a diameter of a fluid supply tube. The catheter irrigation device further includes a flexible linkage supporting the projections and maintaining the projections about the fluid supply tube. The flexible linkage can be depressed to a restricted position in which the space between the projections is reduced to compress the fluid supply tube (i.e., to create an occlusion). The flexible linkage and the projections are also configured to slide along the fluid supply tube in a longitudinal direction.

Longitudinal movement of the catheter irrigation device in the direction of the catheter with the projections in the restricted position forces the fluid within the fluid supply tube in the distal direction to increase the fluidic pressure within the catheter. The fluidic pressure consequently raises to a level sufficient to dislodge the blockage at the distal end of the catheter.

Alternatively, longitudinal movement of the catheter irrigation device in the direction away from the catheter with the projections in the restricted position forces the fluid within the fluid supply tube in the proximal direction to decrease the fluidic pressure within the catheter. The pressure differential across the blockage occurring between the vessel and the catheter cannula increases to a level sufficient to draw the blockage through the catheter cannula and into the fluid supply tube. Thereafter, the fluid supply tube is replaced.

In a preferred embodiment, the projections comprise rollers which are positioned generally parallel to each other and are spaced apart from each other to define a space of sufficient size to receive a diameter of the fluid supply tube connected to the indwelling catheter. The rollers are also configured to roll over the fluid supply tube in a longitudinal direction. The rollers attached to the flexible linkage are positioned such that the axes of the rollers are generally perpendicular to the longitudinal axis of the fluid supply tube.

The flexible linkage desirably comprises a deflectable band configured to receive the fluid supply tube. The band preferably has generally an elliptical cross-sectional shape. The band also defines a pair of opposing holes sized to receive the fluid supply tube. The holes are advantageously positioned such that the fluid supply tube threads through one of the holes, between the projections and out the other hole. The band also extends between a first end and a second end, with the first and second ends being positioned proximate to a major axis of the elliptically shaped band. Alternatively, the band has a continuous cross-sectional shape.

The flexible linkage may additionally include an interengaging element disposed between the ends of the band which interconnects the ends and holds the band in the restricted position. The interengaging element preferably comprises a series of ratchet teeth disposed on the band at one end of the band and a pawl disposed on the other end of the band.

The ratchet teeth/pawl interconnection of the interengaging element holds the band in a several restricted positions as the pawl is adjusted over the ratchet teeth. Thus, the degree of tube occlusion can be varied to throttle the flow through the catheter irrigation device or to substantially block the flow through the device. Thus, the present catheter irrigation device may be used to adjust flow rates through the IV line or may be used to clamp the IV line to substantially stop flow, in addition to being used to irrigate the catheter.

In another preferred embodiment, the projections have an arcuate, convex leading surface which smoothly slide over the fluid supply tube. The projections more preferably comprise semi-cylindrical protuberances. Alternatively, the projections comprise a chamfered surface positioned aft of the arcuate surface and ramping towards the opposing projection to a pinch point.

In accordance with a preferred method of use, a catheter irrigation device is attached to a fluid supply line connected to an indwelling catheter. The catheter irrigation device is deflected to a restricted position in which a pair of projections of the device compress the fluid supply line to create an occlusion in the inner lumen of the fluid supply tube. While maintaining the catheter irrigation device in this position, the device is slid along the fluid supply tube. The catheter irrigation device dislodges the blockage clogging the distal end of the catheter by sliding the device for a sufficient distance to generate enough pressure to dislodge the blockage from the catheter distal end.

BRIEF DESCRIPTION OF THE DRAWINGS

These and other features of the invention will now be described with reference to the drawings of a preferred embodiment which is intended to illustrate and not the limit the invention, and in which:

FIG. 5 is a perspective view of a catheter irrigation device in accordance with another preferred embodiment of the present invention;

FIG. 6 is a perspective view of a catheter irrigation device in accordance with an additional preferred embodiment of the present invention; and FIG. 7 is a perspective view of the catheter irrigation device of FIG. 1 in a restricted position occluding the fluid supply tube.

DETAIL DESCRIPTION OF PREFERRED EMBODIMENTS

Figure 1:
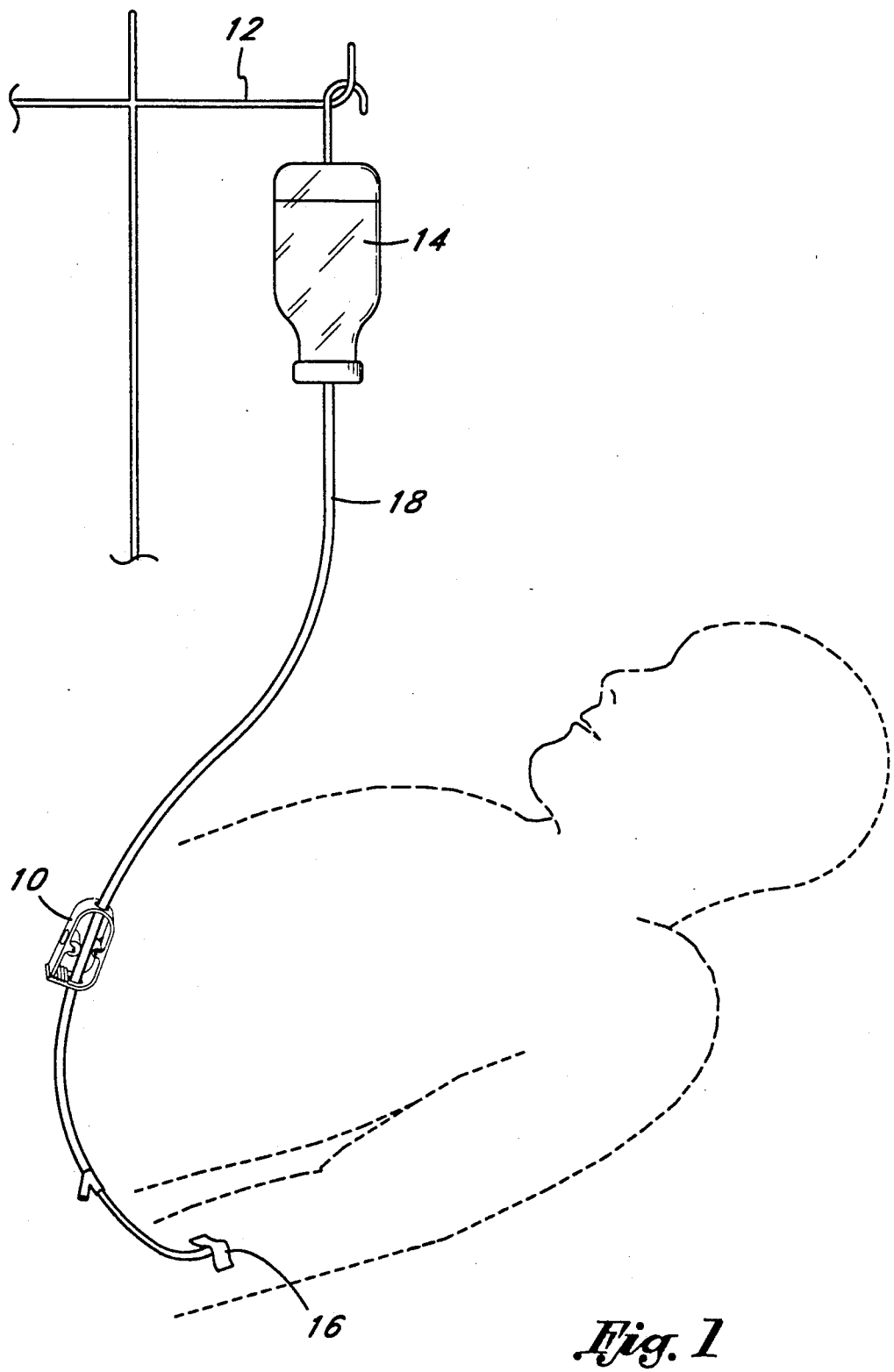
FIG. 1 is a perspective view of a catheter irrigation device in accordance with a preferred embodiment of the present invention coupled to an intravenous catheter line extending between a fluid supply container and an indwelling catheter.

FIG. 1 schematically illustrates a catheter irrigation device 10 connected to a standard catheterization system including a support stand 12, a fluid supply container 14, an indwelling catheter 16 and an intravenous ("IV") line 18 which extends between the fluid supply container 14 and the catheter 16.

The catheter irrigation device 10 readily and unobtrusively attaches to the IV line 18 for easy access when irrigating the catheterization site. Further, as described below, the irrigation device 10 may also double as an adjustable clamp to throttle or cease flow through the IV line 18. In this manner, the irrigation device 10 functionally integrates into the catheterization system between catheter irrigation procedures.

Figure 2:
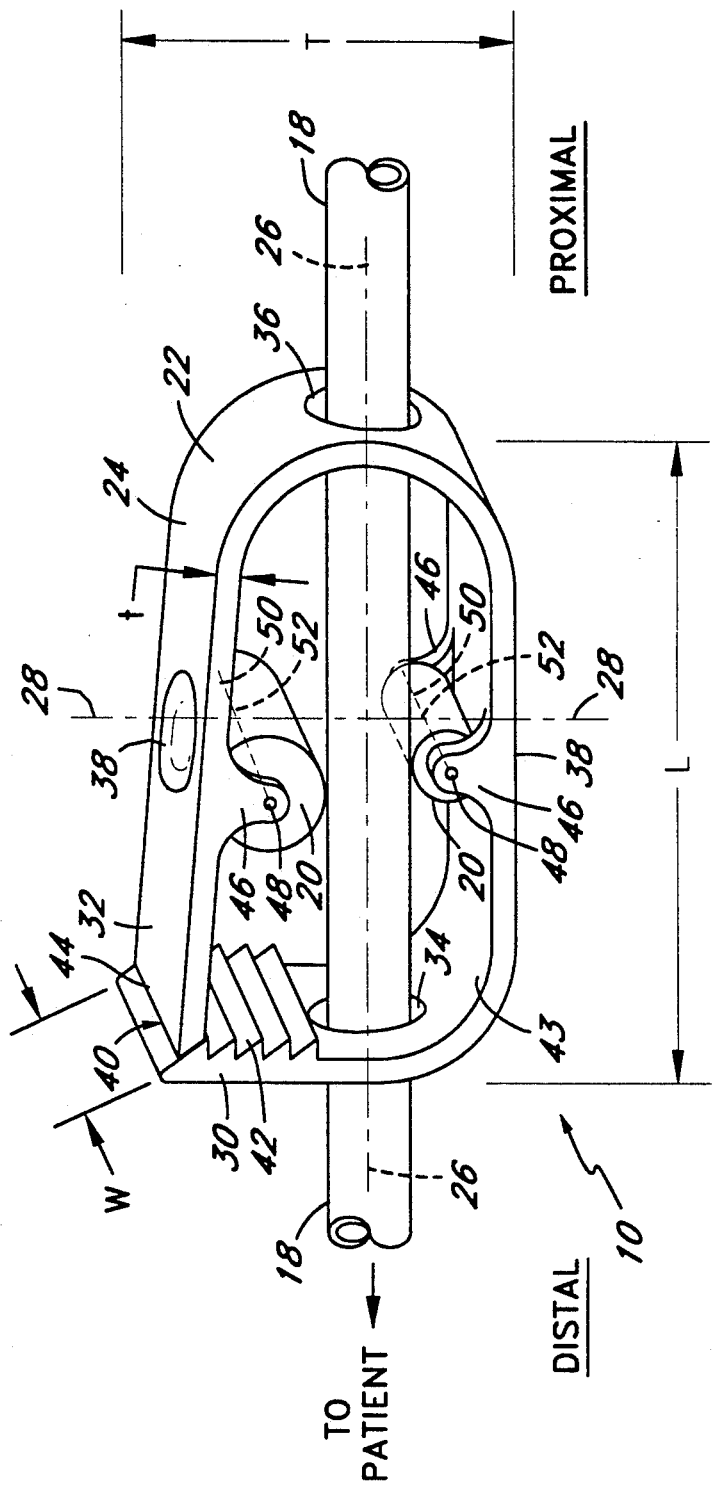
FIG. 2 is an enlarged perspective view of the catheter irrigation device of FIG. 1.

FIG. 2 illustrates in an enlarged perspective view the irrigation device 10 comprising a plurality of opposing rollers 20 supported by a flexible linkage 22. The linkage 22 preferably comprises a deflectable band 24 generally having an elliptical cross-sectional shape which defines a major axis 26 and a minor axis 28. The band 24 extends from a first end 30 and terminates at a second end 32 and has a generally uniform thickness. The band 24 has a width W greater than the diameter of the IV line 18, and preferably has a width W sufficiently large for ergonomic manipulation by the fingers of a nurse or like healthcare provider. The catheter irrigation device 10, in accordance with an embodiment for use with a standard bore IV 18, has a width W of approximately 0.5 inch (1.3 cm), a length L of approximately 1.5 inches (3.8 cm), and an overall thickness T of approximately 1.0 (2.5 cm). As will be readily appreciated by one of skill in the art, irrigation devices incorporating the present invention can be manufactured in any of a wide variety of sizes and configurations in addition to those described herein.

The band 24 defines a forward hole 34 and an aft hole 36 through which the IV line passes. The holes 34, 36 preferably have diameters sufficiently larger than the outer diameter of the IV tube 18 so that the IV tube 18 easily inserts through the holes 34, 36 without the band 24 partially occluding the IV line 18 at the locations of the holes 34, 36. The holes 34, 36 are positioned in the band 24 such that the longitudinal axis of the IV tube 18 lies substantially collinear with the major axis 26 of the band 24.

Proximate to the ends its minor axis 28, the band 24 defines on its outer surface finger indentations 38 which facilitate grasping the irrigation device 10 between a thumb and a forefinger to depress the band 24 towards the IV tube 18, as described below.

As FIG. 2 illustrates, the linkage 22 additionally comprises an interengaging element 40 which interconnects the first end 30 and the second end 32. The interengaging element 40 preferably comprises a plurality of ratchet teeth 42 disposed on an inner surface 43 of the band 24 and positioned proximate to the band first end 30, and a pawl 44 positioned at the band second end 32. The pawl 44 is desirably formed by tapering the thickness t of the band 24 to a thickness less than the pitch (i.e., the peak to peak distance) between the ratchet teeth 42. It is contemplated, however, that other types of interengaging elements 40, such as, for example, snaps, clips and like connectors, would work as well.

The linkage 22 also comprises a plurality of lugs 46, and preferably includes a pair of lugs 46 to support each roller 20. The lugs 46 desirably are integrally formed with the band 24 and extend from the inner surface 43 of the band 24 towards the band's center. Each lug 46 defines an eyelet 48 distanced from the inner surface 43 of the band 24 by at least a distance equal to the radius of the cylindrical roller 20 and sized to receive an axle 50 used to support the roller 20. Each axle 50 extends between a pair of lugs 46, and supports the roller 20. Each pair of lugs 46 is desirably positioned symmetrically about the forward hole 34 and the aft hole 36, and also positioned such that each axle 50 lies generally perpendicular and proximate to the minor axis 28 of the band 24 and lies generally perpendicular to the longitudinal axis of the fluid supply tube 18.

The band 24, lugs 46 and interengaging element 40 of the linkage 22 are preferably integrally formed of a durable, flexible material, and more preferably formed of a generally inert, non-toxic material. In a preferred embodiment, the linkage 22 is molded of plastic, such as, for example, polycarbonate, polyvinylchloride, polypropylene, polyurethane, tetrafluoroethylene (e.g., TEFLON ®), polytetrafluoroethylene (PTEF), acetal resin (e.g., DELRIN ®), chlorotrifluoroethylene (e.g., KEL-F ®), nylon or like polymers.

As FIG. 2 illustrates, the roller 20 generally have cylindrical shapes; however, it is contemplated that any roller with a convex, arcuate surface leading in the direction of rotation (e.g., a spherical shape) would work as well. Each cylindrical roller 20 has a length sufficient to cause an occlusion in the IV line 18 when compressed against the IV line 18, and preferably has a length at least equal to the diameter of the IV line 18 and slightly less than the distance between a pair of lugs 46.

Figure 3:
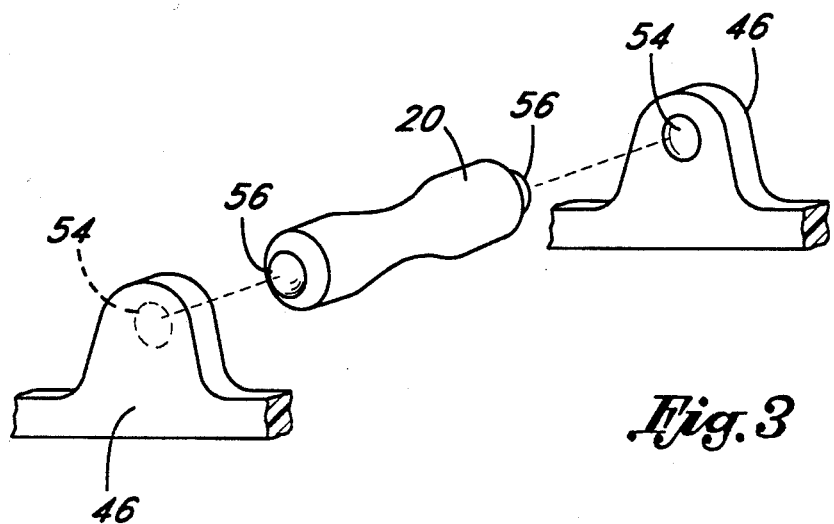
FIG. 3 is a partial exploded perspective view of an interconnection between a roller and a lug in accordance with an additional preferred embodiment of the present invention.
Figure 4:
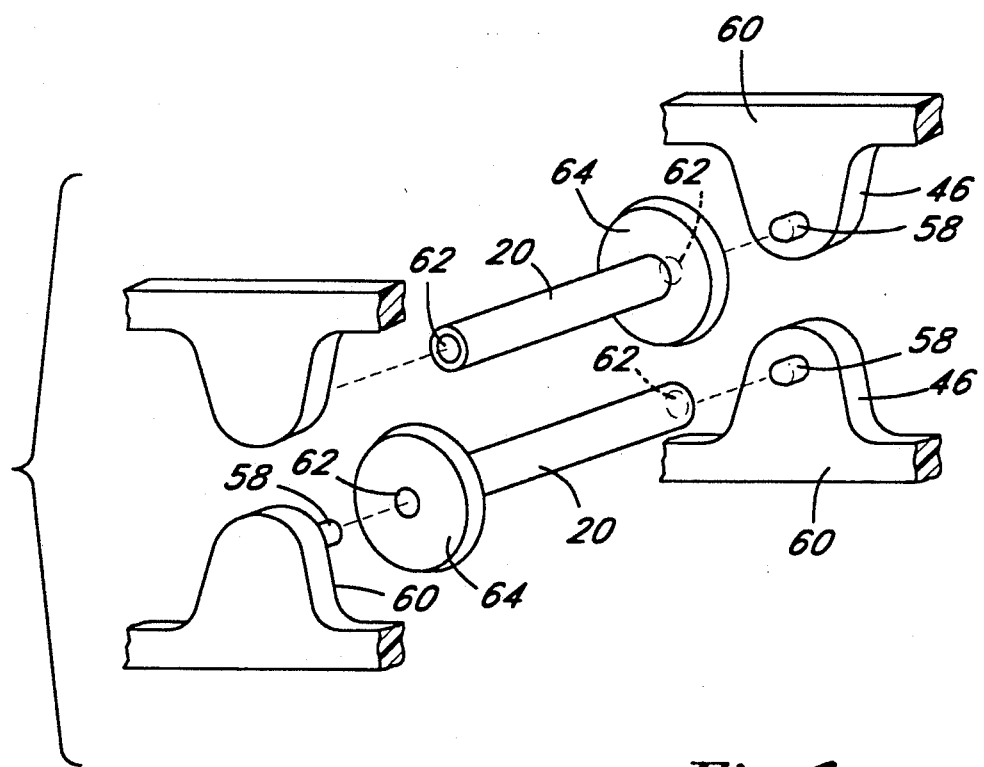
FIG. 4 is a partial exploded perspective view of an interconnection between a roller and a lug in accordance with a further preferred embodiment of the present invention.
Figure 2:
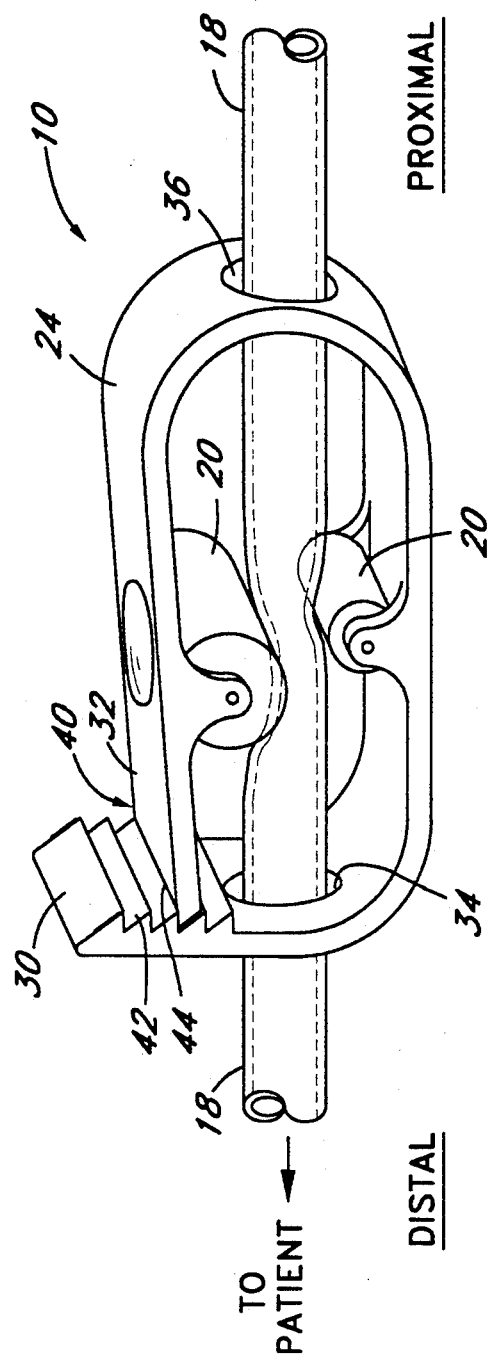

The rollers may also be configured to completely capture the IV tube between the rollers. That is, the rollers may have a generally hour-glass shape, as illustrated in FIG. 3, or may otherwise include flared ends, as illustrated in FIG. 4, to completely capture the IV line between the rollers.

The rollers 20 also define an axial aperture 52 which extends through the roller 20 in a longitudinal direction. The axial aperture 52 receives the axle 50. In this manner, the roller 20 connects to and is supported by the band 24 about the IV tube 18 inserted through the band 24.

As an alternative to the axle 50 supporting the roller 20, the structure of the lugs 46 may support the rollers 20. That is, as illustrated in FIG. 3, the lugs 46 may define opposing sockets 54 which engage a correspondingly shaped ends 56 of roller 20 such that the lugs 46 capture the roller 20 and permit the roller 20 to rotate about the longitudinal axis of the roller 20 within the sockets 54. FIG. 4 shows an alternative embodiment in which a pair of opposing nubs 58 extending from inner surfaces 60 of the lugs 46 and engaging sockets 62 defined by the ends 64 of roller 20. In either of these embodiments, the structure of the lugs 46 support the roller 20.

The rollers 20 are formed of a generally ridge material in order to compress the IV tube 18, and more preferably of a self-lubricating material, such as, for example, tetrafluoroethylene (e.g., TEFLON ®), polytetrafluoroethylene (PTEF), acetal resin (e.g., DELRIN ®), chlorotrifluoroethylene (e.g., KEL-F ®), nylon or like polymers, in order to smoothly slide over the IV line 18.

FIG. 5 illustrates in perspective view a catheter irrigation device 10a in accordance with another preferred embodiment of the present invention attached to an IV line 18a. Where appropriate, like numbers with an "a" suffix have been used to indicate like parts of the first embodiment and the present embodiment for ease of understanding. The irrigation device 10a includes a plurality of opposing protuberances 100 supporting by a flexible linkage 102.

The linkage 102 preferably comprises a deflectable band 24a generally having an elliptical cross-sectional shape which defines a major axis 26a and a minor axis 28a. The band 24a extends from a first end 30a and terminates at a second end 32a, and has a generally uniform thickness. The band 24a has a width greater than the diameter of the IV line 18a, and preferably has a width sufficiently large for ergonomic manipulation by the fingers of a nurse.

The band 24a defines a forward holes 34a and an aft hole 36a through which the IV line 18a passes. The holes 32a, 34a preferably have diameters sufficiently larger than the outer diameter of the IV line 18a so that the IV line 18a easily inserts through the holes 34a, 36a without the band 24 partially occluding the IV line 18a at the locations of the holes 34a, 36a. The holes 34a, 36a are positioned in the band 24a such that the longitudinal axis of the IV tube 18a lies substantially collinear with the major axis 26a of the band 24a.

Proximate to the ends its minor axis 28a, the band 24 defines on its outer surface finger indentations 38a which facilitate grasping the irrigation device 10a between a thumb and a forefinger to depress the band 24a towards the IV tube 18a, as described below.

FIG. 5 also illustrates that the linkage 102 includes an interengaging element 40a which interconnects the first end 30a and the second end 32a. The interengaging element 40 preferably comprises a plurality of ratchet teeth 42a disposed on an inner surface 43a of the band 24a and positioned proximate to the band first end 30a, and a pawl 44a positioned at the band second end 32a. The pawl 44a is formed by tapering the thickness t of the band 24a to a thickness less than the pitch (i.e., the peak to peak distance) between the ratchet teeth 42a.

In the preferred embodiment illustrated in FIG. 5, a pair of protuberances 100 extend from the inner surface 43a of the band 24a toward the band's center. Each protuberance 100 is defined by an arcuate, convex leading surface 104 which smoothly transitions into a chamfered surface 106. The chamfered surface 106 ramps from the leading surface 104 towards the band's center and terminates at a pinch point edge 108.

Each protuberance 100 has a width sufficient to cause an occlusion in the IV line 18a when compressed against the IV line 18a, preferably has a width at least equal to the diameter of the IV line 18a, and more preferably has a width generally equal to the width 18a of the band 24a. Each protuberance 100 also has a thickness (i.e., a distance between the band inner surface 43a and the pinch point edge 108) sufficiently large to occlude the inner lumen of the IV line 108a with the first and second ends 30a, 32a of the band interconnected by the interengaging element 40a. The thickness of each protuberance 100, in accordance with one embodiment, approximately equals 0.25 inch (0.63 cm). However, the dimensions of the protuberance can readily be customized to suit the specific application. The protuberances 100 are positioned such that a longitudinal axis of each protuberance 100 lies generally perpendicular and proximate to the minor axis 28a of the band 24a.

The linkage 102 and protuberances 100 are preferably integrally formed of a durable, flexible material, and more preferably formed of a generally inert, non-toxic material. In a preferred embodiment, the irrigation device 10a is molded of plastic, such as, for example, polycarbonate, polyvinylchloride, polypropylene, polyurethane, tetrafluoroethylene (e.g., TEFLON ®), polytetrafluoroethylene (PTEF), acetal resin (e.g., DELRIN ®), chlorotrifluoroethylene (e.g., KEL-F ®), nylon or like polymers. It is also preferred that the material comprising the protuberances 100 at the pinch points 108 be self-lubricating or be siliconized (or otherwise impregnated with lubrication), in order for the irrigation device 10a to slide smoothly over the IV tube 18a with the protuberances 100 occluding the inner lumen of the IV tube 18a. The pinch points 108 may also or alternatively be lubricated with a lubricant, such as, for example, petroleum jelly.

FIG. 6 illustrates in perspective view a catheter irrigation device 10b in accordance with an additional preferred embodiment of the present invention attached to an IV line 18b. Where appropriate, like numbers with an "b" suffix have been used to indicate like parts of the first embodiment and the present embodiment for ease of understanding. The irrigation device 10b includes a plurality of opposing protuberances 120 supported by a flexible linkage 122.

The linkage 122 preferably comprises a deflectable band 124 generally having an elliptical cross-sectional shape which defines a major axis 26b and a minor axis 28b. The band 124 has a continuous cross-sectional shape with a generally uniform thickness. The band 124 also has a width greater than the diameter of the IV line 18b, and preferably has a width sufficiently large for ergonomic manipulation by the fingers of a nurse or like healthcare provider.

The band 124 defines a pair of reliefs 126 through which the IV line 18b passes. Each relief 126 preferably extends from a side edge 128 of the band 124 and defines a thickness sufficiently larger than the outer diameter of the IV line 18b so that the IV tube 18b easily inserts into the reliefs 126 without the band 124 partially occluding the IV line 18b at the locations of the reliefs 126. Although FIG. 6 illustrates both reliefs 126 extending into the band 124 from the same side edge 128, it should be understood that the reliefs 126 could be positioned on opposite side edges.

The reliefs 126 also have a width sufficiently large such that the reliefs 126 fully receive the IV tube 18b. That is, the IV tube 18a completely fits within the reliefs 126. The reliefs 126 preferably position the IV line 18b collinear with the major axis 26a of the band 124.

Proximate to the ends its minor axis 28b, the band 124 defines on its outer surface finger indentations 38b which facilitate grasping the irrigation device 10b between a thumb and a forefinger to depress the band 124 towards the IV tube 18b, as described below.

As illustrated in FIG. 6, a pair of protuberances 120 extend from the inner surface 43b of the band 124 toward the band's center. Each protuberance 120 generally has a semi-cylindrical shape having a width sufficient to cause an occlusion in the IV line 18b when compressed against the IV line 18b. The protuberances 120 are desirably positioned such that a longitudinal axis of each protuberance 120 lies generally perpendicular and proximate to the minor axis 28b of the band 124. However, those skilled in the art will appreciate that other configurations and orientations will work in addition to the preferred embodiment described herein.

Each protuberance 120 preferably has a width at least equal to the diameter of the IV line 18b, and more preferably has a width generally equal to the width of the band 124. The protuberance 120 also has a thickness (i.e., a distance between the band inner surface 43b and a pinch point 130) sufficiently large to occlude the inner lumen of the IV line 18b when the band 124 is deflected by pressure applied to the finger indentations 38b. The thickness of each protuberance 120, in accordance with one embodiment, approximately equals 0.25 inch (0.63 cm).

The linkage 122 and protuberances 120 are preferably integrally formed of a durable, flexible material, and more preferably formed of a generally inert, non-toxic material. In a preferred embodiment, the irrigation device 10b is molded of plastic, such as, for example, polycarbonate, polyvinylchloride, polypropylene, polyurethane, tetrafluoroethylene (e.g., TEFLON ®), polytetrafluoroethylene (PTEF), acetal resin (e.g., DELRIN ®), chlorotrifluoroethylene (e.g., KEL-F ®), nylon or like polymers. It is also preferred that the material comprising the protuberances 120 at the pinch points 130 be self-lubricating or be siliconized (or otherwise impregnated with lubrication), in order for the irrigation device 10b to smoothly slide over the IV tube 18b with the protuberances 120 occluding the inner lumen of the IV tube 18b. The pinch points 130 may also or alternatively be lubricated with a lubricant, such as, for example, petroleum jelly.

Although FIGS. 3 and 4 illustrate the protuberances as having either a semi-cylindrical or generally ramping cross-sectional shape, it should be understood that other configurations could be used as well so long as the protuberance has an arcuate, convex leading edge which smoothly blends into a pinch point. In addition, it is contemplated that different configurations of protuberances could oppose each other (i.e., the protuberances do not have to be mirror images of each other), and one protuberance could oppose a roller 120. Moreover, one projection (e.g., roller or protuberance) could simply oppose the inner surface 43 of the band 24. It should also be understood that irrigation device could include a plurality of opposing pairs of projections (e.g., roller or protuberances).

The above embodiments also illustrate a few permutations of the flexible linkage 22, 122 which are within the scope of this invention. Thus, rollers 20 could be used with a continuous band 124 which defines holes 34, 36 through which the IV tube 18 passes. Likewise, the irrigation device could comprise a flexible linkage 22 with an interengaging element 40 and a plurality of semi-cylindrical protuberances 120.

To irrigate a catheterization site, a nurse uses the catheter irrigation device 10. The following discussion describes the irrigation process in connection with the embodiment of the irrigation device 10 illustrated in FIGS. 1, 2 and 5; however, it is contemplated that the method of use for the other disclosed embodiments of the irrigation device will be substantially identical, and the discussion herein of one will be understood as applying equally to all, unless specified to the contrary.

Before the IV line 18 is connected to an indwelling catheter 16, the irrigation device 10 is attached to the line 18 by threading the distal end of the line 18 through the aft hole 36, between the rollers 20 (or protuberances) and out the forward hole 34. Alternatively, the IV line 18 can be slipped between the rollers 20 (or protuberances) and into the reliefs 126 from the side edge 128 (as illustrated in FIG. 6) of the irrigation device 10. Thus, the embodiment of the irrigation device 10b illustrated in FIG. 6 can be retrofit to the IV line 18 even with the IV line 18 connected to the indwelling catheter 16.

As illustrated by FIG. 1, the irrigation device 10 may be left permanently attach to the IV line 18 for convenient storage and/or to function as an adjustable clamp, as explained below. If the irrigation device 10 is readily removable once the IV line 18 is connected to an indwelling catheter 16—as is the case with an irrigation device having side reliefs 126—the nurse or healthcare provider can attach the device when irrigating the catheterization site and can remove the irrigation device 10 for personal storage in a pocket.

To irrigate the catheterization site, the nurse slides or positions the irrigation device 10 proximate to the indwelling catheter 16 and preferably on a section of IV line 18 containing liquid. As illustrated in FIG. 7, the nurse then depresses the center of the deflectable band 24 to reduce the spacing between the rollers 20 (or protuberance), causing the rollers 20 (or protuberance) to compress the IV tube 18 and occlude the tube inner lumen. The nurse depresses the band 24 by grasping the irrigation device 10 between his or her forefinger and thumb at the finger indentations 38. The nurse then either holds the band 24 in this restricted position or causes the interengaging element 40 to interconnect the ends 30, 32 of the band 24. In the latter case, the engagement between the pawl 44 and the ratchet teeth 42 of the interengaging element 40 maintains the rollers 20 in this restricted position.

The nurse then slides the irrigation device 10 along the IV tube 18 to alter the pressure within the catheter 16. If the irrigation device 10 includes protuberances 100, the protuberance arcuate surface 104 (see FIG. 5) should lead the protuberance 100 in the direction of travel. By sliding the irrigation device 16 distally, towards the catheter 16, the pressure inside the catheter 16 increases. Alternatively, by sliding the irrigation device 10 proximally, away from the catheter 16, the pressure within the catheter 16 decreases. The irrigation device 10 is slid by a sufficient distance to alter the pressure within the catheter 16 adequately to dislodge the blockage either by forcing the blockage off the distal catheter end and into the body lumen, or by sucking the blockage up through the catheter cannula and into the IV line 18. For use with a standard bore IV line 18, distal displacement of the irrigation device 10 in the range of 2 to 6 inches (5.1 to 15.3 cm) has been found to produce sufficient pressure to dislodge most blockages. After irrigating the catheter 16, the irrigation device 10 can be removed for further use or can be disposed with the spent IV line 18.

The irrigation device 10 illustrated in the embodiment of FIGS. 2 and 4 can also be used to throttle flow or completely clamp off flow in the IV tube 18. The variable positioning of the pawl 44 over the ratchet teeth 42 of the interengaging element 40 provides for varying degrees of band deflection, and thus varying decrease of occlusion of the tube 18 compressed between the rollers 20 (or protuberances). Thus, slight deflection of the band 24 causes minimal occlusion in the IV tube inner lumen, which in turn slightly restricts the flow through the IV tube 18 at the occlusion. However, greater deflection of the band 24 produces greater occlusion which may be increased to a point of completely blocking flow through the IV tube 18. The engagement of the pawl 44 with each ratchet tooth 42 maintains the band 24 in the varying degrees of deflection. Thus, the irrigation device may be used to throttle or cease flow through the IV line 18, as well as being used to irrigate the catheterization site.

FIG. 7 also illustrates the interconnection between the ratchet teeth 42 and the pawl 40 of the interengagement element 40. Because the ratchet teeth 42 slop downwardly, the pawl 44 can be ratcheted towards the IV tube 18 by depressing on the center of the band 24 at the finger indentations 38 to partially or completely occlude the IV tube 18. To disengage the pawl 44 from ratchet teeth 42, the band second end 32 is pulled proximally with a finger positioned in the finger indentation 38, or the band first end 30 is deflected distally by pulling the band first end 30 away from the band second end 32. In this matter, the extent of IV tube occlusion can be decreased or the rollers 20 can be completely disengaged from the IV tube 18 to permit free fluid flow therethrough.

The irrigation device 10 thus integrates effectively with the catheterization system, being readily available when the catheter 16 requires irrigation, being unobtrusively stored on the IV line 18, and being capable of functioning as an adjustable clamp. Moreover, the irrigation device 10 does not expose nurses or healthcare providers to contaminated sharps when irrigating the catheterization site. Furthermore, the irrigation device 10 produces less pressure within the catheterized vessel which reduces both discomfort to the patient and damage to the vessel.

Although this invention has been described in terms of a certain preferred embodiments, other embodiments apparent to those of ordinary skill in the art are also within the scope of this invention. Accordingly, the scope of the invention is intended to be defined only by the claims which follow.

What is claimed is:

1. A method of irrigating or aspirating an indwelling catheter inserted into a body lumen of a patient, to dislodge a blood clot or a like organic debris blockage which has clogged a distal end of the indwelling catheter, said catheter connected to a fluid supply tube, said method comprising the steps of:
   providing a catheter irrigation/aspiration device which comprises a pair of opposing rollers supported by a deflectable band;
   positioning said catheter irrigation/aspiration device over a section of said fluid supply tube which contains fluid and is proximate to said indwelling catheter;
   attaching said catheter irrigation/aspiration device to said fluid supply tube connected to said indwelling catheter;
   deflecting said catheter irrigation/aspiration device to a restricted position in which said opposing rollers on said catheter irrigation/aspiration device compress said fluid supply tube to restrict an inner lumen of said fluid supply tube;
   sliding said catheter irrigation/aspiration device along said fluid supply tube while maintaining said catheter irrigation/aspiration device in said restricted position; and
   dislodging the blockage from the distal end of said indwelling catheter by sliding said catheter irrigation/aspiration device over said fluid supply tube for a sufficient distance to generate enough pressure differential in the fluid to dislodge the blockage.

2. The method of irrigating or aspirating an indwelling catheter as defined by claim 1, wherein said catheter irrigation device is slid along the fluid supply tube for a distance ranging between approximately 2 and 6 inches (5.1 and 15.3 cm).

3. The method of irrigating or aspirating an indwelling catheter as defined by claim 1, wherein said step of attaching said catheter irrigation device to the fluid supply line comprises the steps of threading the fluid supply line through a first hole of said catheter irrigation device, between said pair of projections and out a second hole of said catheter irrigation device.

4. The method of irrigating or aspirating an indwelling catheter as defined by claim 1, wherein said catheter irrigation device is maintained in said restricted position by interconnecting a pair of ends of said catheter irrigation device with an interengaging element.

5. The method of irrigating or aspirating an indwelling catheter as defined by claim 1, wherein said catheter irrigation device is slid distally towards the indwelling catheter to sufficiently increase the pressure within the catheter to force the blockage off the catheter distal end.

6. The method of irrigating or aspirating an indwelling catheter as defined by claim 1, wherein said catheter irrigation device is slid proximally away from the indwelling catheter to sufficiently decrease the pressure within the catheter to draw the blockage through the catheter and into the fluid supply tube.

7. A method of dislodging a blood clot or like organic debris blockage which has clogged a distal end of a catheter indwelling in a body lumen of a patient, said catheter connected to a fluid supply tube, said method comprising the steps of:
   producing a restriction in an inner lumen of said fluid supply tube proximate to an interconnection between said fluid supply tube and said indwelling catheter;
   moving the restriction longitudinally along a length of said fluid supply tube to alter the pressure within said indwelling catheter; and
   dislodging the blockage from the distal end of said indwelling catheter.

8. The method of claim 7, wherein said step of producing a restriction comprises compressing the fluid supply tube.

9. The method of claim 8, wherein said fluid supply tube is compressed between a pair of rollers.

10. The method of claim 7, wherein the restriction is moved distally towards the indwelling catheter to sufficiently increase the pressure within the catheter to force the blockage off the catheter distal end.

11. The method of claim 7, wherein the restriction is moved proximally away from the indwelling catheter to sufficiently decrease the pressure within the catheter to draw the blockage through the catheter.

12. A method of dislodging a blood clot or like organic debris blockage which has clogged a distal end of a catheter indwelling in a body lumen of a patient, said indwelling catheter connected to a fluid supply tube, said method comprising the steps of:
   positioning an irrigation/aspiration device over said fluid supply tube, proximate to said indwelling catheter;
   compressing said fluid supply tube between a pair of opposing projections of said irrigation/aspiration device to produce a restriction in an inner lumen of said fluid supply tube;
   sliding said irrigation/aspiration device longitudinally over said fluid supply tube, in the proximal direction away from said indwelling catheter so as to decrease the pressure within said indwelling catheter; and
   producing a sufficient pressure differential across the blockage at the distal end of said indwelling catheter so as to draw the blockage through said catheter and into said fluid supply line.

13. The method of claim 12 additionally comprising the step of providing a catheter irrigation/aspiration device which comprises a pair of opposing rollers supported by a deflectable band.

14. The method of claim 12, wherein said irrigation/aspiration device is slid over said fluid supply tube for a distance ranging from about 2 inches (5.1 cm) to about 6 inches (15.3 cm).

15. The method of claim 12, additionally comprising the steps of disconnecting said fluid supply tube from said indwelling catheter with the blockage drawn into said fluid supply tube.

16. A method of dislodging a blood clot or like organic debris blockage which has clogged a distal end of a catheter indwelling within a body lumen of a patient, said indwelling catheter connected to a fluid supply tube, said method comprising the steps of:

positioning an irrigation/aspiration device over said fluid supply tube, proximate to said indwelling catheter;

compressing said fluid supply tube between a pair of opposing projections of said irrigation/aspiration device to produce a restriction in an inner lumen of said fluid supply tube;

sliding said irrigation/aspiration device longitudinally over said fluid supply tube in the distal direction toward said indwelling catheter so as to increase the pressure within said indwelling catheter; and producing a sufficient pressure differential across the blockage at the distal end of said indwelling catheter so as to force the blockage off the distal end of said catheter.

17. The method of claim 16, additionally comprising the step of providing a catheter irrigation/aspiration device which comprises a pair of opposing projections supported by a deflectable band.

18. The method of claim 17, additionally comprising the step of applying a lubricant to said projections of said catheter irrigation/aspiration device.

19. The method of claim 17, wherein said projections are rollers

20. The method of claim 16, additionally comprising the step of threading a portion of said fluid supply tube between said pair of opposing projections of said catheter irrigation/aspiration device.

21. The method of claim 16, wherein said irrigation/aspiration device is slid over said fluid supply tube for a distance ranging from about 2 inches (5.1 cm) to about 6 inches (15.3 cm).

* * * * *